United States Patent
Adjei et al.

[11] Patent Number: 6,136,294
[45] Date of Patent: Oct. 24, 2000

[54] AMINO ACID STABILIZED MEDICAL AEROSOL FORMULATION

[75] Inventors: Akwete Adjei; Anthony J. Cutie, both of Bridgewater, N.J.

[73] Assignee: Aeropharm Technology Inc.

[21] Appl. No.: 09/158,369

[22] Filed: Sep. 22, 1998

[51] Int. Cl.[7] .......................................... A61L 9/04
[52] U.S. Cl. ............................................. 424/45; 424/489
[58] Field of Search ................................................ 424/45

[56] References Cited

U.S. PATENT DOCUMENTS

| | | |
|---|---|---|
| 2,868,691 | 1/1959 | Porush et al. . |
| 2,885,427 | 5/1959 | Ruh et al. . |
| 3,261,748 | 7/1966 | Larsen . |
| 4,129,603 | 12/1978 | Bell . |
| 4,174,295 | 11/1979 | Bargigia et al. . |
| 5,126,123 | 6/1992 | Johnson . |
| 5,182,097 | 1/1993 | Byron et al. . |
| 5,190,029 | 3/1993 | Byron et al. . |
| 5,225,183 | 7/1993 | Purewal et al. ............................ 424/45 |
| 5,254,330 | 10/1993 | Ganderton et al. . |
| 5,439,670 | 8/1995 | Purewal et al. . |
| 5,569,450 | 10/1996 | Duan et al. . |
| 5,605,674 | 2/1997 | Purewal et al. . |
| 5,653,962 | 8/1997 | Akehurst et al. . |
| 5,658,549 | 8/1997 | Akehurst et al. . |
| 5,674,471 | 10/1997 | Akehurst et al. . |
| 5,674,472 | 10/1997 | Akehurst et al. .......................... 424/45 |
| 5,676,929 | 10/1997 | Akehurst et al. . |
| 5,676,931 | 10/1997 | Adjei et al. . |
| 5,683,676 | 11/1997 | Akehurst et al. . |
| 5,683,677 | 11/1997 | Purewal et al. . |
| 5,688,782 | 11/1997 | Neale et al. . |
| 5,695,743 | 12/1997 | Purewal et al. . |
| 5,720,940 | 2/1998 | Purewal et al. . |
| 5,725,841 | 3/1998 | Duan et al. . |
| 5,736,124 | 4/1998 | Akehurst et al. . |
| 5,744,123 | 4/1998 | Akehurst et al. . |

FOREIGN PATENT DOCUMENTS 0518600   12/1992   European Pat. Off. .

Primary Examiner—Thurman K. Page
Assistant Examiner—P. E. McQueeney
Attorney, Agent, or Firm—Frommers Lawrence & Haug

[57] ABSTRACT

This invention relates to a medicinal aerosol formulation and more particularly, to a medicinal aerosol formulation containing a particulate drug, a propellant and a stabilizing agent selected from an amino acid, an amino acid derivative and a mixture of the foregoing.

26 Claims, No Drawings

AMINO ACID STABILIZED MEDICAL AEROSOL FORMULATION

BACKGROUND OF THE INVENTION

1. Field of the Invention

This invention relates to a medicinal aerosol formulation, and more particularly, to a medicinal aerosol formulation comprising a stabilizer selected from an amino acid, a derivative thereof or a mixture of the foregoing.

2. Description of the Related Art

Delivery of drugs to the lung by way of inhalation is an important means of treating a variety of conditions, including such common local conditions as bronchial asthma and chronic obstructive pulmonary disease and some systemic conditions including pain management, cystic fibrosis, etc. Steroids, β2 agonists, anti-cholinergic agents, proteins and polypeptides are among the drugs that are administered to the lung for such purposes. Such drugs are commonly administered to the lung in the form of an aerosol of particles of respirable size (less than about 10 $\mu$m in diameter). In order to assure proper particle size in the aerosol, particles can be prepared in respirable size and then incorporated into a suspension formulation containing a propellant. Alternatively, formulations can be prepared in solution form in order to avoid the concern for proper particle size in the formulation. Solution formulations must nevertheless be dispensed in a manner that produces particles or droplets of respirable size.

Once prepared an aerosol formulation is filled into an aerosol canister equipped with a metered dose valve. In the hands of the patient the formulation is dispensed via an actuator adapted to direct the dose from the valve to the patient.

It is important that an aerosol formulation be stable such that the pressurized dose discharged from the metered dose valve is reproducible. Rapid creaming, settling, or flocculation after agitation are common sources of dose irreproducibility in suspension formulations. This is especially true where a binary aerosol formulation containing only medicament and propellant, e.g. 1,1,1,2-tetrafluoroethane, is employed or where such formulation contains small amounts of surfactant as well. Sticking of the valve also can cause dose irreproducibility. In order to overcome these problems aerosol formulations often contain surfactants, which serve as suspending aids to stabilize the suspension for a time sufficient to allow for reproducible dosing. Certain surfactants also function as lubricants to lubricate the valve to assure smooth actuation. Myriad materials are known and disclosed for use as dispersing aids in aerosol formulations. Suitability of materials, however, is dependent on the particular drug and the propellant or class of propellant used in the formulation.

It is sometimes difficult to dissolve sufficient quantities of conventional surfactants in hydrofluorocarbon (HFC) propellants such as HFC-134a and HFC-227. Cosolvents, such as ethanol, have been used to overcome this problem, as described in U.S. Pat. No. 5,225,183. An alternative approach that avoids cosolvents involves materials that are soluble in hydrofluorocarbon propellants and are said to be effective surfactants or dispersing aids in an aerosol formulation. Among such materials are certain fluorinated surfactants and certain polyethyoxysurfactants.

SUMMARY OF THE INVENTION

It has surprisingly been found that novel medicinal aerosol formulations can be obtained without the use of either cosolvents, such as ethanol, or surfactants, such as sorbitan trioleate which are added to a binary aerosol formulation. Stable medicinal aerosol formulations are obtained by the use of amino acids, derivatives thereof or a mixture of the foregoing.

DETAILED DESCRIPTION OF THE INVENTION

This invention involves a stable suspension aerosol formulation suitable for pressurized delivery which comprises (1) a particulate medicament or drug, (2) a suitable propellant, and (3) a suitable stabilizer.

A suitable medicament or drug is one which is suitable for administration by inhalation, the inhalation being used for oral and nasal inhalation therapy. Therapeutic categories of drugs or medicaments include cardiovascular drugs, antiallergics, analgesics, brochodilators, antihistamines, antitussives, antifungals, antivirals, antibiotics, pain medicaments, antiinflammatories, peptides, proteins and steroids.

Particularly suitable medicaments or drugs include albuterol (also known as salbutamol), atropine, beclomethasone, esters of beclomethasone such as its monopropionate and dipropionate, budesonide, cromolyn, epinephrine, ephedrine, fentanyl, flunisolide, formoterol, ipratropium bromide, isoproterenol, pirbuterol, prednisolone, salmeterol, amiloride fluticasone, fluticasone esters, such as phosphate, monohydrate and furoate, (−)4-amino-3,5-dichloro-α-[[[6(2-pyridinyl)ethoxy]hexyl]amino]methyl]benzene-methanol. Also included are the suitable acid addition salts of the foregoing drugs, their hydrates and their other solvates. In this regard, suitable acid addition salts include the salts obtained from inorganic acids, such as hydrochloric, hydrobromic, sulfuric, nitric, phosphoric and perchloric acids as well as organic acids such as tartaric, citric, acetic, succinic, maleic, fumaric and oxalic acids. Suitable pharmaceutically acceptable solvates include solvates with ethylactate, alkanes, ethers, alcohols and water.

For purposes of the formulations of this invention, which are intended for inhalation into the lungs, the medicament or drug is preferably micronized whereby a therapeutically effective amount or fraction (e.g., ninety percent or more) of the drug is particulate. Typically, the particles have a diameter of less than about 10 microns, and preferably less than about 5 microns, in order that the particles can be inhaled into the respiratory tract and/or lungs.

The particulate medicament or drug is present in the inventive formulations in a therapeutically effective amount, that is, an amount such that the drug can be administered as an aerosol, such as topically, or via oral or nasal inhalation, and cause its desired therapeutic effect, typically preferred with one dose, or through several doses. The particulate drug is administered as an aerosol from a conventional valve, e.g., a metered dose valve.

The term "amount" as used herein refers to quantity or to concentration as appropriate to the context. The amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors. Generally a therapeutically effective amount will be from about 0.005 parts by weight to about 2 parts by weight based on 100 parts by weight of the propellant.

A suitable propellant is selected. A suitable propellant is any fluorocarbon, e.g. a 1–4 hydrogen containing flurocarbon(, such as $CHF_2CHF_2$, $CF_3CH_2F$, $CH_2F_2CH_3$ and $CF_3CHFCF_3$), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants such as mixtures of propellants 11, 12 and 114. Non-CFC propellants such as 1,1,1,2-tetrafluoroethane (Propellant 134a), 1,1,1,2,3,3,3-heptafluoropropane (Propellant 227) or mixtures thereof are preferred. The propellant is preferably present in an amount sufficient to propel a plurality of the selected doses of drug from an aerosol canister.

A suitable stabilizer is selected. A suitable stabilizer includes (1) an amino acid selected from (a) a monoamino carboxylic acid of the formula, $H_2N—R—COOH$ (I), (b) a monoamino dicarboxylic acid of the formula, $H_2N—R(COOH)_2$ (II) and (c) a diamino monocarboxylic acid of the formula $(H_2N)_2—R\ COOH$ (III), where R is a straight or branched alkyl radical of from 1 to 22 carbon atoms, which can be mono or poly-substituted with moieties such as sulfide (—S—), oxide (—O—), hydroxyl (_OH), amide (—NH), sulfate (_SO4); aryl of the formula

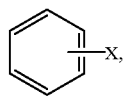

where X is hydrogen, halogen (F, Cl, BR, I), alkyl of 1 to 6 carbon atoms, alkoxy of 1 to 6 carbon atoms, hydroxy and nitro; and heterocyclic, such as thienyl, furyl, pyranyl, imidazolyl, pyrrolyl, thizolyl, oxazolyl, pyridyl, and pyrimidinyl compounds; (2) a derivative of the amino acid selected from (a) acid addition salts of the amino group, obtained from inorganic acids, such as hydrochloric, hydrobromic, sulfuric, nitric, phosphoric, and perchloric acids, as well as organic acids, such as tartaric, citric, acetic, succinic, maleic, fumaric, oxalic acids; (b) amides of the carboxylic acid group, e.g., glutamine, (c) esters of the carboxylic acid group obtained from aliphatic straight or branched chain alcohols of from 1 to 6 carbon atoms, e.g. L-aspartyl-L-phenylalanine methylester (Aspartame®), and (3) a mixture of the amino acid and the derivative of the amino acid.

Suitable amino acids of the formula I include glycin, glycine, alanine, valine, leucine, isoleucine, methionine, threonine, isovaline, phenylalanine, tyrosine, serine, cysteine, N-acetyl-L-cysteine, histidine, tryptophan, proline, and hydroxyproline, e.g. trans-4-hydroxy proline. Compounds of the formula II include, aspartic acid, and glutamic acid, compounds of the formula (III) include arginine, lysine, hydroxylysine, ornithine, asparagine, and citrulline.

An aerosol formulation preferably comprises the stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about two or three seconds after agitation.

The particular amount of stabilizer that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the stabilizer can be present in a formulation in an amount from about 0.000002 percent by weight, to about 20% by weight, more preferably about 0.0002 percent to about 10% by weight, based on the weight of the formulation.

It has surprisingly been found that the formulation of the invention is stable without the necessity of employing a cosolvent, such as ethanol, or surfactants. However, further components, such as conventional lubricants or surfactants, cosolvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety.

Generally the formulations of the invention can be prepared by combining (i) the drug in an amount sufficient to provide a plurality of therapeutically effective doses; (ii) the stabilizer in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular stabilizer and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, coated or uncoated, anodized or unanodized, e.g., those of aluminum, glass, stainless steel, polyethylene terephthalate, and coated canisters or cans with epon, epoxy, etc., can be used to contain a formulation of the invention.

The formulation of the invention can be delivered to the respiratory tract and/or lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, (local) or diabetes (systemic), or they can be delivered via topical (e.g., buccal) administration in order to treat, e.g., angina or local infection.

What is claimed is:

1. A medicinal aerosol formulation, which comprises:
   (a) a therapeutically effective amount of a particulate medicament;
   (b) a propellant; and
   (c) a stabilizer selected from an amino acid, a derivative thereof, or a mixture of the foregoing.

2. The formulation as defined in claim 1 wherein said stabilizer is selected from the group consisting of glycin, glycine, alanine, valine, leucine, isoleucine, methionine, threonine, isovaline, phenylalanine, tyrosine, serine, histidine, tryptophan, proline, hydroxyproline, arginine, ornithine, asparagine, citrulline, aspartic acid, cysteine, glutamic acid, glutamine, lysine, hydroxylysine, N-acetyl-L-cysteine, phenylalanine, trans-4-hydroxy-L-proline, tyrosine, L-aspartyl-L-phenylalanine methylester and a mixture of any of the foregoing.

3. The formulation as defined in claim 1 wherein the medicament is selected from the group consisting of albuterol, atropine, beclomethasone, beclomethasone monopropionate, beclomethasone dipropionate, budesonide, cromolyn, epinephrine, ephedrine, fentanyl, flunisolide, formoterol, ipratropium bromide, isoproterenol, pirbuterol, prednisone, salmeterol, amiloride, fluticasone, fluticasone esters, (−)4-amino-3,5-dichloro-α-[[[6(2-pyridinyl)ethoxy]hexyl]amino]methyl]benzene-methanol and pharmaceutically acceptable salts, esters, hydrates and solvates of the foregoing.

4. The formulation as defined in claim 1, wherein said propellant is selected from the group consisting of 1,1,1,2-tetrafluoroethane, 1,1,1,2,3,3,3-heptafluoropropane or a mixture thereof.

5. The formulation as defined in claim 1 which further includes a cosolvent.

6. The formulation as defined in claim 5 wherein said cosolvent comprises ethanol.

7. The formulation as defined in claim 2 wherein said stabilizer is present in an amount effective to prevent settling, creaming or flocculation of the formulation for a time sufficient to allow reproducible dosing of the drug after agitation of the formulation.

8. The formulation as defined in claim 7 wherein said stabilizer is present in an amount ranging from about 0.000002% by weight to about 20% by weight based on the weight of the formulation.

9. A method of preparing a medicinal aerosol formulation according to claim 1, which comprises:
   (a) combining (i) said medicament in an amount sufficient to provide a plurality of therapeutically effective doses, (ii) said propellant in an amount sufficient to propel a plurality of said therapeutically effective doses from an aerosol canister; and (iii) said stabilizer in an amount effective to stabilize the formulation; and
   (b) dispersing components (i), (ii) and (iii).

10. The method as defined in claim 9 wherein the medicinal aerosol formulation further comprises combining in step (a) a cosolvent and in step (b) dispersing components (i), (ii), (iii) with said cosolvent.

11. A method of treating in an animal a condition capable of treatment by oral or nasal inhalation, which comprises, administering a formulation according to claim 1 to said animal by oral or nasal inhalation.

12. A formulation according to claim 1 in an aerosol canister equipped with a metered dose valve.

13. A method of stabilizing a suspension aerosol formulation comprising a propellant and a particulate drug which comprises,
   incorporating into the formulation a stabilizer selected from the group consisting of a suitable amino acid, a derivative thereof, or any mixture of the foregoing, in an amount which is effective to prevent settling, creaming, or flocculation of the formulation for a time sufficient to allow reproducible dosing of the drug after agitation of the formulation.

14. A metered dose inhaler containing a medicinal aerosol formulation, the formulation comprising:
   (a) a drug in particulate form in a therapeutically effective amount;
   (b) a propellant; and
   (c) a suitable stabilizer selected from an amino acid, an amino acid derivative, or a mixture of the foregoing, present in an amount sufficient to stabilize the formulation to prevent settling, creaming or flocculation for a time sufficient to allow reproducible dosing of the drug after agitation of the formulation.

15. The metered dose inhaler as defined in claim 14 wherein the stabilizer is selected from the group consisting of glycin, glycine, alanine, valine, leucine, isoleucine, methionine, threonine, isovaline, serine, histidine, tryptophan, proline, hydroxyproline, arginine, ornithine, asparagine, citrulline, aspartic acid, cysteine, glutamic acid, glutamine, lysine, hydroxylysine, N-acetyl-L-cysteine, phenylalanine, trans-4-hydroxy-L-proline, tyrosine, L-aspartyl-L-phenylalanine methylester and a mixture of any of the foregoing.

16. The metered dose inhaler as defined in claim 15 wherein said stabilizer is present in an amount of 0.000002% by weight to about 20% by weight based on the weight of the medicinal aerosol formulation.

17. The metered dose inhaler as defined in claim 14 wherein the drug is selected from the group consisting of albuterol, atropine, beclomethasone, beclomethasone monopropionate, beclomethasone dipropionate, budesonide, cromolyn, epinephrine, ephedrine, fentanyl, flunisolide, formoterol, ipratropium bromide, isoproterenol, pirbuterol, prednisone, salmeterol, amiloride, fluticasone, an ester of fluticasone,(−)4-amino-3,5-dichloro-α-[[[6(2-pyridinyl)ethoxy]hexyl]amino]methyl]benzene-methanol and pharmaceutically acceptable hydrates, salts and solvates of the foregoing.

18. The metered dose inhaler as defined in claim 14 wherein the propellant is selected from the group consisting of 1,1,1,2-tetrafluoroethane, 1,1,1,2,3,3,3-heptafluoropropane or a mixture thereof.

19. The metered dose inhaler as defined in claim 14 wherein the medicinal aerosol formulation further comprises a cosolvent.

20. The metered dose inhaler as defined in claim 19 wherein said cosolvent comprises ethanol.

21. A medicinal aerosol formulation as defined in claim 1, which comprises
   (a) a therapeutically effective amount of a particulate medicament;
   (b) a propellant
   (c) a stabilizer, in addition to the medicament, selected from an amino acid, a derivative thereof or a mixture of the foregoing.

22. A medicinal aerosol formulation as defined in claim 1, which comprises
   (a) a therapeutically effective amount of a particulate medicament selected from the group consisting of albuterol, atropine, beclomethasone, beclomethasone monopropionate, beclomethasone dipropionate, budesonide, cromolyn, epinephrine, ephedrine, fentanyl, flunisolide, formoterol, ipratropium bromide, isoproterenol, pirbuterol, prednisone, salmeterol, amiloride, fluticasone, fluticasone esters, (−)4-amino-3,5-dichloro-α-[[[6(2-pyridinyl)ethoxy]hexyl]amino]methyl]benzene-methanol and pharmaceutically acceptable salts, esters, hydrates and solvates of the foregoing;

(b) a hydrofluoro carbon propellant; and (c) from about 0.000002% by weight to about 20% by weight, based on the weight of the formulation, of a stabilizer selected from the group consisting of
  (1) an amino acid which is
    (a) a monoamino carboxylic acid of the formula, $H_2N-R-COOH$ (I)
    (b) a monoamino dicarboxylic acid of the formula $H_2N-R(COOH)_2$ (II) and
    (c) a diamino monocarboxylic acid of the formula $(H_2N)_2-R\ COOH$ (III),
  where R is a straight or branched alkyl radical of from 1 to 22 carbon atoms, which is optionally mono- or polysubstituted with a sulfide, oxide, hydroxyl, amide, sulfate or aryl of the formula

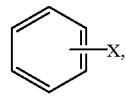

where X is hydrogen, halogen, alkyl of 1 of 6 carbon atoms, hydroxy, nitro, or a thienyl-, furyl- pyranyl-, imidazolyl-, pyrrolyl-, thizolyl-, oxazolyl-, pyridyl-, a pyrimidinyl-containing heterocyclic compound;

(2) a derivative of the amino acid selected form (a) an inorganic or organic acid addition salt of the amino group of the amino acid, or (b) an amide of the carboxylic acid group of the amino acid; and (3) a mixture of the amino acid and the derivative of the amino acid.

23. The formulation as defined in claim 22, wherein the stabilizer is selected from the group consisting of glycin, glycine, alanine, valine, leucine, isoleucine, methionine, threonine, isovaline, phenylalanine, tyrosine, serine, histidine, tryptophan, proline, hydroxyproline, arginine, ornithine, asparagine, citrulline, aspartic acid, cysteine, glutamic acid, glutamine, lysine, hydroxylysine, N-acetyl-L-cysteine, phenylalanine, trans-4-hydroxy-L-proline, tyrosine, L-aspartyl-L-phenylalanine methylester and a mixture of any of the foregoing.

24. The formulation as claimed in claim 1, wherein the medicament is fluticasone.

25. The formulation as claimed in claim 1, wherein the medicaments are fluticasone and an anticholinergic agent.

26. The metered dose inhaler wherein the drug is fluticasone or fluticasone and an anticholinergic agent.

* * * * *

US006136294C1

(12) REEXAMINATION CERTIFICATE (4647th)
United States Patent
Adjei et al.

(10) Number: US 6,136,294 C1
(45) Certificate Issued: Sep. 24, 2002

(54) AMINO ACID STABILIZED MEDICAL AEROSOL FORMULATION

(75) Inventors: Akwete Adjei; Anthony J. Cutie, both of Bridgewater, NJ (US)

(73) Assignee: Aeropharm Technology Incorporated, Edison, NJ (US)

Reexamination Request:

No. 90/006,032, Jun. 8, 2001

Reexamination Certificate for:

| | |
|---|---|
| Patent No.: | 6,136,294 |
| Issued: | Oct. 24, 2000 |
| Appl. No.: | 09/158,369 |
| Filed: | Sep. 22, 1998 |

(51) Int. Cl.[7] ........................ A61K 9/12; A61K 31/195; A61L 9/04

(52) U.S. Cl. ............................ 424/45; 424/489; 424/46

(58) Field of Search ............................ 424/45, 46, 489

(56) References Cited

U.S. PATENT DOCUMENTS

| | | | | |
|---|---|---|---|---|
| 5,225,183 | A | 7/1993 | Purewal et al. | |
| 5,594,015 | A | 1/1997 | Kurtz et al. | 514/369 |
| 5,635,159 | A | 6/1997 | Lu et al. | |
| 6,193,954 | B1 | 2/2001 | Adjei et al. | |

FOREIGN PATENT DOCUMENTS

| | | |
|---|---|---|
| WO | WO 90/09781 | 2/1990 |

*Primary Examiner*—Mina Haghghatian

(57) ABSTRACT

This invention relates to a medicinal aerosol formulation and more particulary, to a medicinal aerosol formulation containing a particulate drug, a propellant and a stabilizing agent selected from an amino acid, an amino acid derivative and a mixture of the foregoing.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5, 6, 10, 19, 20 are cancelled.

Claims 1, 13, 14, 21, 22 and 26 are determined to be patentable as amended.

Claims 2–4, 7–9, 11, 12, 15–18 and 23–25, dependent on an amended claim, are determined to be patentable.

1. A medicinal aerosol formulation, which [comprises] *consists essentially of*:
   (a) a therapeutically effective amount of a particulate medicament;
   (b) a propellant; and
   (c) a stabilizer selected from an amino acid, a derivative thereof, or a mixture of the foregoing
   *whereby said medicament and said stabilizer are different.*

13. A method [of] *for* stabilizing a suspension aerosol formulation comprising a propellant and a particulate drug which comprises,
   incorporating into the formulation a stabilizer selected from the group consisting of a suitable amino acid, a derivative thereof, or any mixture of the foregoing, in an amount which is effective to prevent settling, creaming, or flocculation of the formulation for a time sufficient to allow reproducible dosing of the drug after agitation of the formulation
   *whereby said medicament and said stabilizer are different.*

14. A metered dose inhaler containing a medicinal aerosol formulation, the formulation [comprising] *consisting essentially of*:
   (a) a drug in particulate form in a therapeutically effective amount;
   (b) a propellant; and
   (c) a suitable stabilizer selected from an amino acid, an amino acid derivative, or a mixture of the foregoing, present in an amount sufficient to stabilize the formulation to prevent settling, creaming or fluocculation for a time sufficient to allow reproducible dosing of the drug after agitation of the formulation
   *whereby said medicament and stabilizer are different.*

21. A medicinal aerosol formulation as defined in claim 1, which [comprises] *consists essentially of*
   (a) a therapeutically effective amount of a particulate medicament;
   (b) a propellant
   (c) a stabilizer, in addition to the medicament, selected from an amino acid, a derivative thereof, or a mixture of the foregoing.

22. A medicinal aerosol formulation as defined in claim 1, which [comprises] *consists essentially of*
   (a) a therapeutically effective amount of a particulate medicament selected from the group consisting of albuterol, atropine, beclomethasone, beclomethasone monopropionate, beclomethasone dipropionate, budesonide, cromolyn, epinephrine, ephedrine, fentanyl, flunisolide, formoterol, ipratropium bromide, isoproterenol, pirbuterol, prednisone, salmeterol, amiloride, fluticasone, fluticasone esters, (−)4-amino-3,5-dichloro-α-[[[6(2-pyridinyl)ethoxy]hexyl]amino]methyl]benzene-methanol and pharmaceutically acceptable salts, esters, hydrates and solvates of the foregoing;
   (b) a hydrofluorocarbon propellant; and
   (c) from about 0.000002% by weight to about 20% by weight, based on the weight of the formulation, of a stabilizer selected from the group consisting of
   (1) an amino acid which is
      (a) a monoamino carboxylic acid of the formula, $H_2N—R—COOH$ (I)
      (b) a monoamino dicarboxylic acid of the formula $H_2N—R(COOH)_2$ (II) and
      (c) a diamino monocarboxylic acid of the formula $(H_2N)_2—R\ COOH$ (III),
   where R is a straight or branched alkyl radical of from 1 to 22 carbon atoms, which is optionally mono- or polysubstituted with a sulfide, oxide, hydroxyl, amide, sulfate or aryl of the formula

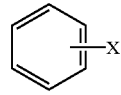

where X is hydrogen, halogen, alkyl of 1 to 6 carbon atoms, hydroxy, nitro, or a thienyl-, furyl- pyranyl-, imidazolyl-, pyrrolyl-, thizolyl-, oxazolyl-, pyridyl-, a pyrimidinyl-containing heterocyclic compound;
   (2) a derivative of the amino acid selected [form] *from*
      (a) an inorganic or organic acid addition salt of the amino group of the amino acid, or (b) an amide of the carboxylic acid group of the amino acid; and
   (3) a mixture of the amino acid and the derivative of the amino acid.

26. The metered dose inhaler *as defined in claim 14* wherein the drug is fluticasone or fluticasone and an anticholinergic agent.

* * * * *